United States Patent
Brandt

(10) Patent No.: US 10,814,186 B2
(45) Date of Patent: Oct. 27, 2020

(54) PORTABLE TENNIS BALL TESTING DEVICE

(71) Applicant: Richard A. Brandt, New York, NY (US)

(72) Inventor: Richard A. Brandt, New York, NY (US)

(*) Notice: Subject to any disclaimer, the term of this patent is extended or adjusted under 35 U.S.C. 154(b) by 0 days.

(21) Appl. No.: 16/748,307

(22) Filed: Jan. 21, 2020

(65) Prior Publication Data

US 2020/0254313 A1  Aug. 13, 2020

Related U.S. Application Data

(60) Provisional application No. 62/803,968, filed on Feb. 11, 2019.

(51) Int. Cl.
| | |
|---|---|
| *A63B 47/00* | (2006.01) |
| *G01N 3/42* | (2006.01) |
| *G01N 33/00* | (2006.01) |
| *A63B 102/02* | (2015.01) |
| *G01B 5/00* | (2006.01) |

(52) U.S. Cl.
CPC ............. *A63B 47/008* (2013.01); *G01N 3/42* (2013.01); *A63B 2102/02* (2015.10); *G01B 5/0023* (2013.01); *G01N 2033/008* (2013.01)

(58) Field of Classification Search
CPC ... A63B 47/008; A63B 2102/02; A63B 60/42; A63B 2039/006; A63B 37/0003; G01B 5/0023; G01N 2033/008; G01N 2203/0019; G01N 2203/0076
See application file for complete search history.

(56) References Cited

U.S. PATENT DOCUMENTS

| | | | | |
|---|---|---|---|---|
| 1,819,232 A | * | 8/1931 | Cropper ................ | G01M 99/00 73/790 |
| 1,874,780 A | * | 8/1932 | McGuckin ............... | G01N 3/00 73/161 |
| 2,049,644 A | * | 8/1936 | Essen ....................... | G01N 3/00 73/161 |
| 2,189,653 A | * | 2/1940 | Luthe ............... | G05D 23/27537 200/83 P |
| 2,278,416 A | * | 4/1942 | Atti ....................... | G01M 99/00 73/818 |

(Continued)

FOREIGN PATENT DOCUMENTS

| | | | |
|---|---|---|---|
| SU | 483597 A1 | * 12/1975 | |
| WO | WO-2017165479 A1 | * 9/2017 | ........... A63B 47/008 |

OTHER PUBLICATIONS

Andrew DeWolfe et al., "Tennis Ball Compression Deformation Testing", ADMET, Jan. 11, 2010. (Year: 2010).*

(Continued)

*Primary Examiner* — David A. Rogers

(74) *Attorney, Agent, or Firm* — R. Neil Sudol; Henry D. Coleman

(57) ABSTRACT

A portable device for determining whether a tennis ball is compliant with a stated deformation standard compresses a tennis ball by application of a pre-determined pre-load followed by a pre-determined force. A scale is provided for measuring the deformation of the tennis ball after it is compressed. The device includes several plate members disposed in parallel and relatively movable a controllable amount by a shifting mechanism.

19 Claims, 7 Drawing Sheets

(56) References Cited

U.S. PATENT DOCUMENTS

| | | | | |
|---|---|---|---|---|
| 2,406,793 A * | 9/1946 | Benkoe | B23Q 17/22 | 33/710 |
| 2,628,496 A * | 2/1953 | Wick | G01M 99/00 | 73/818 |
| 3,376,734 A * | 4/1968 | Ether | G01N 3/40 | 73/78 |
| 3,470,737 A * | 10/1969 | Fridley | G01N 33/025 | 73/81 |
| 3,600,814 A * | 8/1971 | Smith | G01B 3/00 | 33/506 |
| 3,665,757 A * | 5/1972 | Hoag | A63B 47/008 | 73/818 |
| 3,932,977 A * | 1/1976 | Ringler | A63B 39/04 | 53/403 |
| 4,022,469 A * | 5/1977 | Lacoste | A63B 39/06 | 473/606 |
| 4,114,350 A * | 9/1978 | Snyder | A63B 39/04 | 156/145 |
| 4,116,047 A * | 9/1978 | Hejkal | G01N 3/42 | 73/81 |
| 4,154,095 A * | 5/1979 | Snyder | A63B 39/04 | 73/744 |
| 4,313,289 A * | 2/1982 | Birdsong, Jr. | A63B 39/04 | 53/79 |
| 4,555,028 A * | 11/1985 | Valehrach | A63B 47/008 | 209/599 |
| 4,610,166 A * | 9/1986 | Elder | B29C 65/8207 | 73/818 |
| 4,876,658 A * | 10/1989 | Hass | G01N 35/00 | 702/82 |
| 5,222,391 A * | 6/1993 | Reenstra | A63B 47/008 | 73/81 |
| 5,291,774 A * | 3/1994 | Putnam, Jr. | G01N 3/42 | 73/82 |
| 5,321,976 A * | 6/1994 | Dalrymple | G01N 3/42 | 73/81 |
| 5,511,410 A * | 4/1996 | Sherts | G01N 3/14 | 73/81 |
| 5,567,870 A * | 10/1996 | Harris | G01N 3/42 | 73/81 |
| 5,639,969 A * | 6/1997 | D'Adamo | G01N 3/40 | 73/790 |
| 5,672,809 A * | 9/1997 | Brandt | G01N 3/52 | 124/65 |
| 5,760,312 A * | 6/1998 | MacKay | G01N 3/42 | 73/81 |
| 5,837,889 A * | 11/1998 | Slenker | A63B 47/008 | 73/81 |
| 6,196,073 B1 * | 3/2001 | Harding | A63B 47/008 | 73/862.381 |
| 6,357,282 B1 * | 3/2002 | Benjamin | A63B 47/008 | 73/81 |
| 6,360,613 B1 * | 3/2002 | Iggulden | A63B 47/008 | 73/820 |
| 6,612,182 B1 * | 9/2003 | Iggulden | A63B 47/008 | 73/820 |
| 6,755,085 B1 * | 6/2004 | Kazanjian | G01N 3/08 | 73/824 |
| 6,978,671 B1 * | 12/2005 | Meggs | G01F 23/20 | 177/180 |
| 8,371,154 B2 * | 2/2013 | Brandt | G01N 3/08 | 73/78 |
| 8,752,419 B2 * | 6/2014 | Brandt | G01N 3/08 | 73/78 |
| 9,310,283 B2 * | 4/2016 | Niemeyer, III | A63B 47/008 | |
| 9,551,638 B2 * | 1/2017 | Brandt | G01N 3/42 | |
| 9,651,465 B2 * | 5/2017 | Donahue | A63B 47/008 | |
| 9,862,795 B2 * | 1/2018 | Hanson, Jr. | C08G 18/6674 | |
| 9,868,039 B2 * | 1/2018 | Brandt | A63B 60/42 | |
| 2001/0032504 A1 * | 10/2001 | Moseley | G01G 17/04 | 73/290 R |
| 2006/0049207 A1 * | 3/2006 | Bogoshian | A47J 47/01 | 222/196 |
| 2008/0156120 A1 * | 7/2008 | D'Ambrosio | G01N 17/004 | 73/865.6 |
| 2009/0120201 A1 * | 5/2009 | Mendoza | G01N 3/08 | 73/818 |
| 2010/0326201 A1 * | 12/2010 | Brandt | G01N 3/42 | 73/818 |
| 2012/0166106 A1 * | 6/2012 | Niemeyer, III | G01N 3/08 | 702/43 |
| 2013/0118269 A1 * | 5/2013 | Brandt | G01N 3/42 | 73/818 |
| 2014/0150564 A1 * | 6/2014 | Brandt | G01N 3/08 | 73/818 |
| 2016/0296813 A1 * | 10/2016 | Brandt | A63B 60/42 | |

OTHER PUBLICATIONS

Ryan Carmichael, "Tennis Ball Stiffness and Durability", Dec. 19, 2008. (Year: 2008).*

Richard John Dignall, "Modelling the Impact of Tennis Balls on Court Surfaces", The University of Sheffield, Apr. 2004. (Year: 2004).*

* cited by examiner distances in inches

PORTABLE TENNIS BALL TESTING DEVICE

CROSS-REFERENCE TO RELATED APPLICATION

This application claims the benefit of U.S. Provisional Patent Application No. 62/803,968 filed Feb. 11, 2019.

BACKGROUND OF THE INVENTION

This invention relates to method and apparatus for assessing tennis balls to determine whether ball pressure is adequate. Concomitantly, this invention relates to method and apparatus to determine whether ball pressure confirms to officially promulgated rules.

The International Tennis Federation (ITF) tennis ball deformation standard restricts the deformation of compliant (type 1) new balls as follows. When the ball is compressed between two flat parallel plates, after an initial 3.5 lb (15.57 N) preload force is applied, an additional 18 lb (80.07 N) applied force causes the ball to compress an additional distance that is in the range 0.50-0.60 cm (0.197-0.236 in). In addition, after the ball is further compressed to 1 in (2.54 cm) and the applied force is then reduced back to 18 lb, the deformation of the ball must be in the range 0.67-0.91 cm (0.264-0.358 in). The ITF ball standard also restricts the size, weight, and bounce of compliant balls. (The bounce requirement is a limit on the coefficient of restitution (COR) of the ball. The COR is the ratio v'/v of the rebound speed v' and the incident speed v, in a perpendicular impact of the ball on a solid flat surface. It quantifies the liveliness of the ball.)

The ITF tests balls for compliance to this standard using a sophisticated electronic computer-controlled device. Other equally complicated testing devices have been proposed and patented. (For example, H. Hass, U.S. Pat. No. 4,876,658). Such devices are, however, much too expensive, heavy, and complicated to be used courtside. (Chair Umpires often use a tape measure to confirm that the net height is correct, but they have no way to confirm that the available balls are compliant.) There is therefore a need for a portable ball-testing device that is lightweight, reliable, accurate, durable, inexpensive, and easy to use courtside.

After new tennis balls are removed from their pressurized container, they immediately begin to degrade in both elasticity and performance, the more so as the balls are struck by racquets. This degradation occurs because of the decrease in the ball's internal pressure and deterioration of the ball's rubber shell. A sufficiently degraded ball will play and feel very differently from a compliant ball. Players and officials therefore attempt to determine if a ball has become too soft by squeezing or bouncing the ball, but such procedures are obviously highly inaccurate and incapable of determining the small pressure decreases that can adversely affect performance. A more precise ball testing method is clearly needed, but there is currently no courtside device that can accurately implement the ITF testing procedure to determine if a used ball has degraded enough to effect play. Furthermore, there is no ITF standard that states when a ball used in a tournament should be discarded. There is therefore a need for a portable device that can be used to quickly and accurately measure the deformation of a used ball, and for a new ITF standard that specifies when a used ball should be removed from play in a match.

The invention disclosed herein is a class of devices that resolve both of the above deficiencies. In a preferred embodiment, the device tests balls by compressing them in series with a spring of known size and elasticity. This device can implement the complete ITF test for new balls, and the proposed test for used balls. The preload (currently 3.5 lbs) is applied by the weight of the spring and adjoining compression plates, and the subsequent applied force (currently 18 lbs) is exerted by compressing the spring a predetermined distance. With this force applied, the deformation of the ball is measured by a simple adjustable pointer and ruler attached to the device, and the measured value can be compared to the allowable deformation range (or to an allowable range for used balls). The ball can then be further compressed to a stated distance (currently 1 in), as measured on the ruler, and then the applied force can be reduced back to 18 lbs in order to confirm that the measured return deformation lies within the allowable range.

One of the inventive features of the invention is the novel incorporation of the 3.5 lb preload. The preload is crucial since without it a ball's deformation could not be precisely measured because the deformation zero-line could not be accurately determined. The zero-line must be set after the preload is applied, and the deformation distance must be measured relative to that line after the 18 lb force is applied. Any attempt to measure the deformation distance without first applying a preload would be inaccurate because the zero-line, and therefore the measured distance, would depend on the ball's diameter, properties of the ball's rubber shell, the size and nature of the ball's fuzziness, and the ball's internal pressure.

PRIOR ART

A variety of relatively simple ball-testing devices have been proposed and patented. Although each of these devices is capable of determining if a defined measure of a ball's forced deformation has increased from an earlier value, none of them measure deformation as specified by the ITF standard, or are capable of testing for compliance with this standard. In particular, none of these devices incorporate the 3.5 lb preload or subsequent 18 lb force required by the ITF standard, and none have the ability to perform the return deformation measurement required by the ITF standard. Examples are given in the following.

A. Reenstra (U.S. Pat. No. 5,222,391) discloses a device that compresses a ball a fixed distance by rotating a pivoted plate onto the ball and measuring the applied force on the ball using an electronic force sensor placed under the ball. This operation differs that specified by the ITF as follows: the applied force is not perpendicular and is not set at 18 lbs, the compression distance is not set to 1 in or even measured, there is no 3.5 lb preload, and there is no adjustment for ball size. C. Putnam (U.S. Pat. No. 5,291,774) discloses a device that compresses a ball by rotating a pivoted 6 lb plate onto the ball and measuring the consequent deformation of the ball. This operation differs that specified by the ITF as follows: the applied force is not perpendicular and is not set at 18 lbs, the compression distance is not set to 1 in, there is no 3.5 lb preload, and there is no adjustment for ball size. C. Sherts (U.S. Pat. No. 5,511,410) discloses a device that indents a ball with a small cylinder by applying a force to a spring attached to the cylinder. The indentation distance, but not the magnitude of the applied force, is measured. This operation differs that specified by the ITF as follows: the compressing force is not applied by a plate and is not set at 18 lbs, the compression distance is not set to 1 in, there is no 3.5 lb preload, and there is no adjustment for ball size. W. Harris (U.S. Pat. No. 5,567,870) discloses a hand-grip that compresses a ball between curved surfaces when the arms of the grip are brought together. A force gauge is attached to the outer side of the compressing end of the grip, and a plunger attached to the gauge proceeds into the ball through a hole in one of the curved surfaces, so that the gauge displays the force that the indented ball exerts on the plunger. This operation differs that specified by the ITF as follows: the compression force is not applied by a plate and is not set at 18 lbs, the compression distance is much less than the required 1 in, there is no 3.5 lb preload, and there is no adjustment for ball size. Also, the force required to indent an already compressed ball is measured instead of the force required to compress a ball. B. D'Adamo (U.S. Pat. No. 5,639,869) discloses a device that compresses a spring onto a ball in order to force the ball through a constriction in a tube. The distance that the spring compresses in order to accomplish this is measured and used to indicate the state of the ball. This operation differs that specified by the ITF as follows: the applied force is not applied by a plate and is not set at 18 lbs, the compression distance is not the required 1 in, there is no 3.5 lb preload, and there is no adjustment for ball size. Also, the actual force on the ball being tested depends on the elasticity of the ball, making the comparisons of different balls problematic. S. Slenker (U.S. Pat. No. 5,837,889) discloses a device that compresses a ball held in a socket with a probe attached to a flexible arm that is depressed down in order to force the probe into the ball. The shape of the depressed arm is indicated on a scale and is claimed to indicate the state of the ball. This operation differs that specified by the ITF as follows: the applied force is not applied by a plate and is not set at 18 lbs or even measured, the compression distance is not the required 1 in or even measured, there is no 3.5 lb preload, and there is no adjustment for ball size. Also, the actual force on the ball being tested depends on the elasticity of the ball, and the orientation of the measurement scale depends on the compression distance, both making the comparisons of different balls problematic.

For the reasons stated, none of the above ball testing devices are capable of determining if a tested ball is compliant with the ITF standard, nor do they claim to be. (They are able to determine the degree to which the deformation of a given used ball, as measured using the disclosed device instead of using the ITF protocol, has increased from a previous value.) On the other hand, R. Benjamin (U.S. Pat. No. 6,357,282) does disclose a device that is claimed to indicate if a ball meets the USTA standard. (The USTA standard is essentially equivalent to the ITF standard.) The disclosed devices compress a ball in series with a spring, as is done in the present invention, but without the incorporation of the elements necessary to test for compliance with the standard. The compression distance of the ball-spring system is indicated, but not the individual distances, so neither the force exerted on the ball nor the deformation distance of the ball is measured. (Even if the individual distances were measured, the force on the ball, required to be 18 lbs, would not be known since the elasticity of the spring is not specified.) Also, the compressing plate moves a fixed distance, compressing both the ball and the spring, but since the spring compression distance is not fixed, the force exerted on the ball is unknown and is not independent of the ball's elasticity or size, making it impossible test for compliance or to accurately compare different balls. Furthermore, there is no 3.5 lb preload, no return deformation measurement capability, and no adjustment for ball size. (This patent correctly points out defects in the prior art. It states, for example, that the Slenker patent "fails to identify the balls with the proper pressure to meet the standard", but this patent is equally deficient in this regard.)

SUMMARY OF THE INVENTION

A portable device for determining whether a tennis ball is compliant with a stated deformation standard comprises, in accordance with the present invention, a means for compressing a tennis ball by application of a pre-determined pre-load followed by a pre-determined force, a means for measuring the deformation of the tennis ball after it is compressed, and a means for compressing the tennis ball to a pre-determined distance.

Pursuant to another feature of the present invention, the portable device comprises a frame, a rigid first plate member and a rigid second plate member, and a shifting mechanism. The first plate member and the second plate member are disposed in substantially parallel relationship to one another and mounted to the frame so that the first plate member is movable alternately towards and away from the second plate member. The tennis ball is compressible between the first plate member and the second plate member under a predetermined preliminary load. The shifting mechanism is operatively coupled with the first plate member for shifting the first plate member toward the second plate member to exert an additional force of predetermined magnitude on the tennis ball. The first means for compressing and the second means for compressing each include the first plate member and the second plate member, while the means for measuring includes a measuring device with a scale providing a visual indication of an amount of deformation of the tennis ball, the measuring device being mounted at least indirectly to the frame.

In accordance with another feature of the present invention, the shifting mechanism includes an elastic element or spring of preselected elasticity operatively coupled to the first plate member and disposed in linear alignment with the first plate member and the second plate member. The elastic element or spring may take the form of a compression spring disposed on a side of the first plate member opposite the second plate member. Preferably, the testing device then further includes at least one stop element mounted at least indirectly to the frame so as to limit a compression of the compression spring to a fixed predetermined distance resulting in application of the additional force of the predetermined magnitude.

The shifting mechanism may further include a rigid third plate member and a rod, the third plate member being fixed to the frame on a side of the elastic element or spring opposite the first plate member and the rod traversing a hole in the third plate member. Preferably, the rod and the hole have mating threads so that the rod is rotatable and transversely translatable relative to the third plate member.

Pursuant to a further feature of the present invention, the stop element takes the form or one or more rods of equal height extending perpendicularly relative to the first plate and parallel to an axis of compression of the elastic element or spring.

Pursuant to a particular embodiment of the present invention, the measuring device includes a ruler oriented perpendicularly to the first plate member and the second plate member, the ruler being attached to one of the first plate member and the second plate member, while the measuring device further includes a perpendicular rod adjustably attached to the other of the first plate member and the second plate member so as to be movable transversely to the first plate member and the second plate member. The perpendicular rod may be threaded and rotatably traverse a threaded hole in the other of the first plate member and the second plate member, so that the perpendicular rod moves transversely to the other of the first plate member and the second plate member upon a rotation of the perpendicular rod. Also, the perpendicular rod may be provided with a pointer in the form of an elongate arm or a disk attached to the perpendicular rod and extending in a plane perpendicular to an axis thereof.

In accordance with an alternative specific embodiment of the present invention, the shifting mechanism includes a rack and pinion mechanism, with a lever arm attached to the pinion and a perpendicular compressing plate adjacent to the lower end of the rack.

In accordance with another alternative or modified embodiment of the invention, the measuring device includes a mechanical distance gauge attached at least indirectly to the frame. The gauge has a face with a pointer indicating a distance index on a scale extending around a perimeter of the gauge. The gauge also has a retractable measurement plunger extending from a distance measurement dial to a bottom of the first plate member.

A portable device for use in determining whether a tennis ball complies with a pre-established deformation standard comprises, in accordance with the present invention, (i) a frame including a plurality of support rods extending in parallel relationship with one another, (ii) a first plate and a second plate fixed to the support rods and disposed in spaced relationship to one another, (iii) a ball-compressing sliding component disposed between the first plate and the second plate, including an elastic element or spring characterized by a monotonic force vs. distance function $F(x)$, (iv) means for moving the sliding component so as to compress both the elastic element or spring and a ball inserted between the second plate and one of the third plate and the fourth plate, (v) means for limiting a compression distance of the elastic element or spring to $d=F^{-1}(f)$, where the force $f=F(d)$ required to compress the spring the distance d has a predetermined value, and (vi) means mounted at least indirectly to the support rods for measuring a degree or deformation or compression of the ball. The ball-compressing sliding component preferably includes a third plate and a fourth plate coupled to the support rods for mutually independent sliding motion along the support rods, the elastic element or spring being of predetermined height and disposed between and in contact with the third plate and the fourth plate.

Pursuant to another feature of the present invention, the sliding component has a total weight w less than or equal to a specified preload p, with the preload increased to p by compressing the elastic element or spring a measured compression distance $d1=F^{-1}(p-w)$, so that the total preload becomes $w+F(d1)=p$.

In accordance with a further feature of the invention, a downwardly directed rod is attached to the upper one of the third plate and fourth plate and serves for measuring the compression distance d1. The downwardly directed rod has a pointer at a lower end pointing toward a vertical ruler attached to a lower one of the third plate and the fourth plate. The downwardly directed rod and the pointer are configured so that the pointer points to a zero-distance line on the ruler before the elastic element or spring is compressed, the ruler being marked with a distance d1 so that the preload force is specified preload p when the elastic elements or spring is compressed the distance d1, as indicated by the pointer pointing to the d1 line.

According to an additional feature of the invention, the means for limiting the compression distance of the elastic element or spring includes one or more stopping rods that extend upwards from the lower of the third plate and the fourth plate to a height that is a distance d1+d2 below an upper end of the elastic element or spring, where $$d2=F^{-1}(p+f-w)-d1,$$

so that the force on the ball when the spring compression terminates on the stopping rods is $F(d1+d2)+w=p+f$, the specified applied force value when the ball compression distance is measured to test for compliance with the stated standard.

In accordance with the present invention, the means for moving the sliding component may include a rod traversing a hole in the first plate, the rod having one end in force-transmitting engagement with the third plate, the hole being coaxial with the elastic element or spring.

The means for limiting the spring compression distance may include one or more stopping rods attached to one of the third plate and the fourth plate and extending towards the other of the third plate and the fourth plate, where the one or more stopping rods have a length preselected so as to arrest relative motion of the third plate and the fourth plate upon compression of the elastic element or spring by a predetermined distance d.

The means for measuring the deformation of the ball may include a measuring rod movably traversing a hole in the lower of the third and fourth plates, where the measuring rod is provided with a pointer in the form of an elongate arm or a disk attached to the measuring rod and extending in a plane perpendicular to an axis thereof.

In a particular embodiment of the present invention, the sliding component has a weight of a predetermined value equal to a specified preload and the support rods are oriented vertically, while the first plate, the second plate, the third plate and the fourth plate ail extend in respective horizontal planes in parallel to each other.

In accordance with a further feature of the invention, the device further comprises a measuring rod attached to the third plate and extending towards the fourth plate for measuring a compression distance of the elastic element or spring, the measuring rod being provided at one end with a pointer. An elongate marker member is attached to the fourth plate and extends toward the third plate. The elongate marker member is provided with a zero-distance mark, the pointer is aligned with the zero-distance mark prior to compression of the elastic element or spring, and the elongate marker member is further provided with a distance d1 mark, so that a preload force takes on a predetermined initial value upon a compressing of the elastic element or spring the distance d1, as indicated by the pointer pointing to the distance d1 marker.

The means for moving the sliding component may include a rack and pinion mechanism including a rotatable pinion attached to an upper one of the first plate and the second plate and further including a lever arm attached to the rotatable pinion. The rack and pinion mechanism also includes a rack movable through a hole in the upper one of the first plate and the second plate so that a lower end of the rack is engageable with an upper surface of an upper one of the third plate and the fourth plate to move same downwardly.

A method for determining whether a tennis ball is compliant with a predetermined deformation standard comprises, in accordance with the present invention, uses a device including a frame, a rigid first plate member and a rigid second plate member, first plate member and the second plate member being disposed in substantially parallel relationship to one another and mounted to the frame so that the first plate member is movable alternately towards and away from the second plate member. The method includes inserting the tennis ball between the first plate member and the second plate member, thereupon moving the first plate member towards the second plate member to place the tennis ball under a predetermined preliminary load, shifting the first plate member further toward the second plate member to exert an additional force of predetermined magnitude on the tennis ball, and visually reading an indicator position relative to a scale element mounted to the frame, the indicator position providing an indication of an amount of deformation of the tennis ball.

The visual reading of the indicator position may include setting a pointer on a rod at a zero-distance mark on the scale element before the tennis ball is compressed, and reading a position of the pointer on the scale element after the tennis ball is compressed. The scale element may be provided with a first additional mark for a specified minimum compliant ball compression distance when a specified force is applied to the tennis ball, a second additional mark for a maximum compliant distance, a third additional mark for a specified minimum compliant ball compression distance when the specified force is applied to the tennis ball after the tennis ball is compressed a specified distance, and a fourth additional mark for a specified maximum distance when the specified force is applied to the tennis ball after the tennis ball is been compressed the specified distance.

DETAILED DESCRIPTION

Figure 1A:
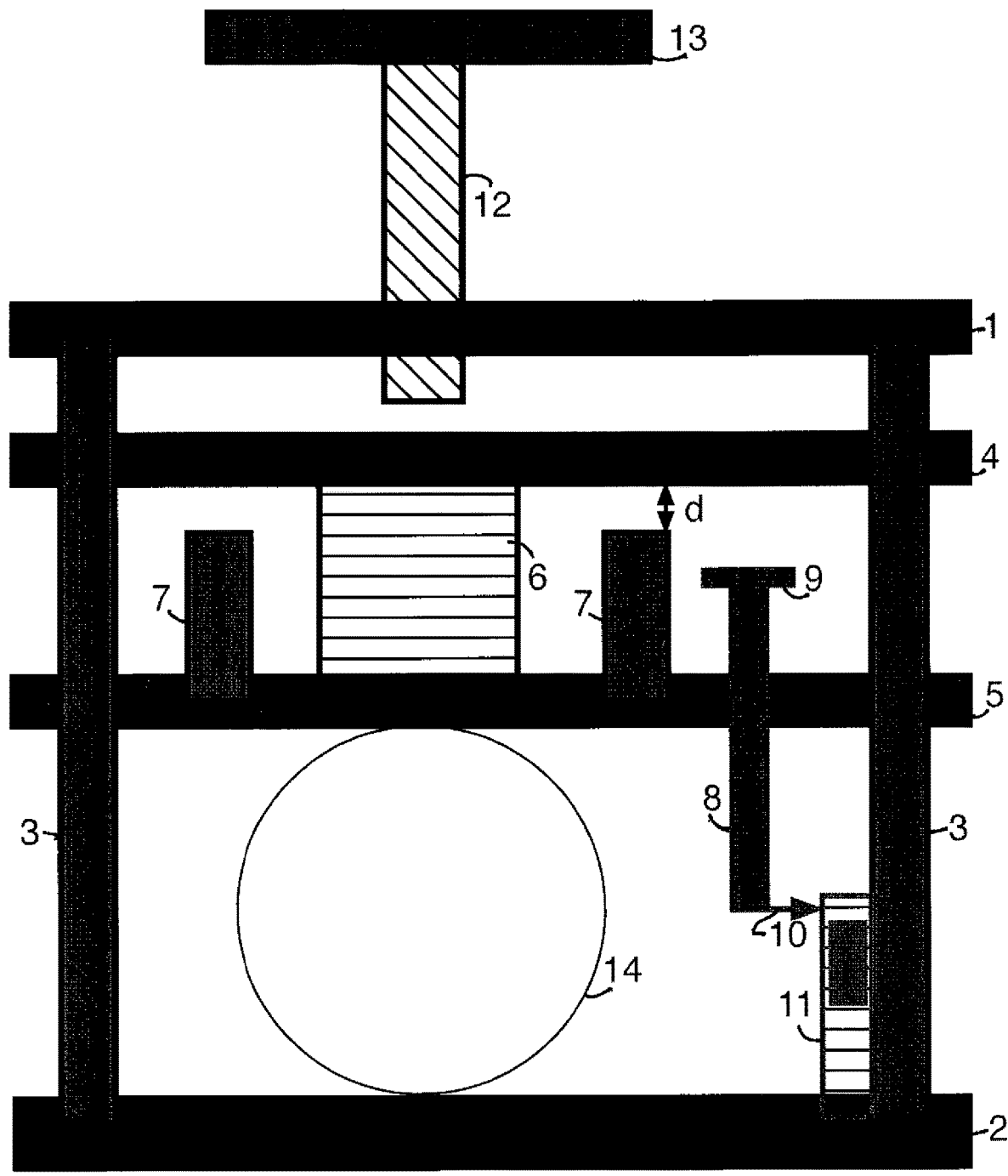
FIG. 1a is a schematic side elevational view of a first embodiment of a portable device for testing a tennis ball for compliance with predetermined deformation standards, in accordance with the present invention, showing the testing device at one stage of a testing procedure.
Figure 1B:
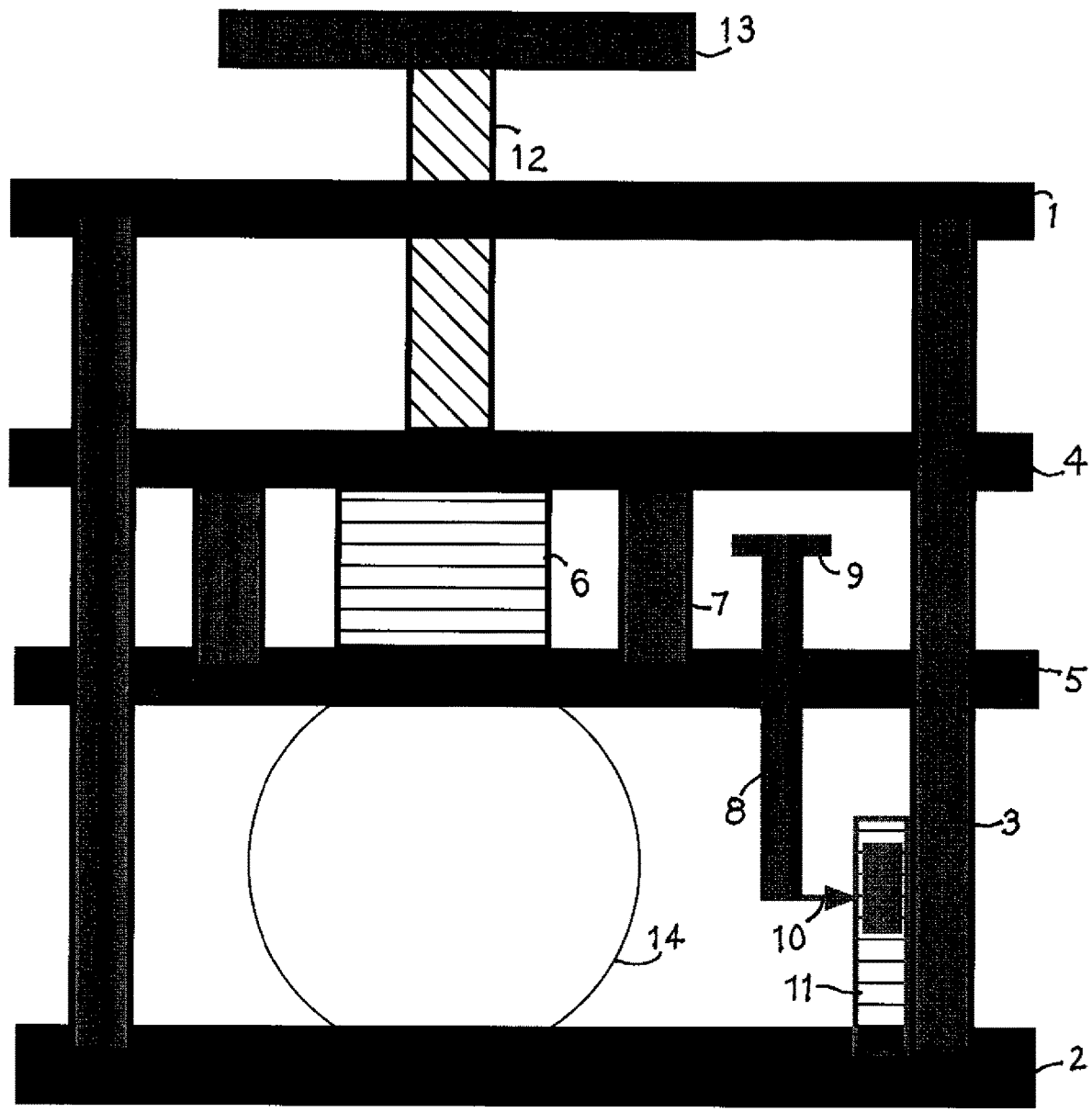
FIG. 1b is a view similar to FIG. 1a, showing the device of FIG. 1a at a different stage of a testing procedure.
Figure 1C:
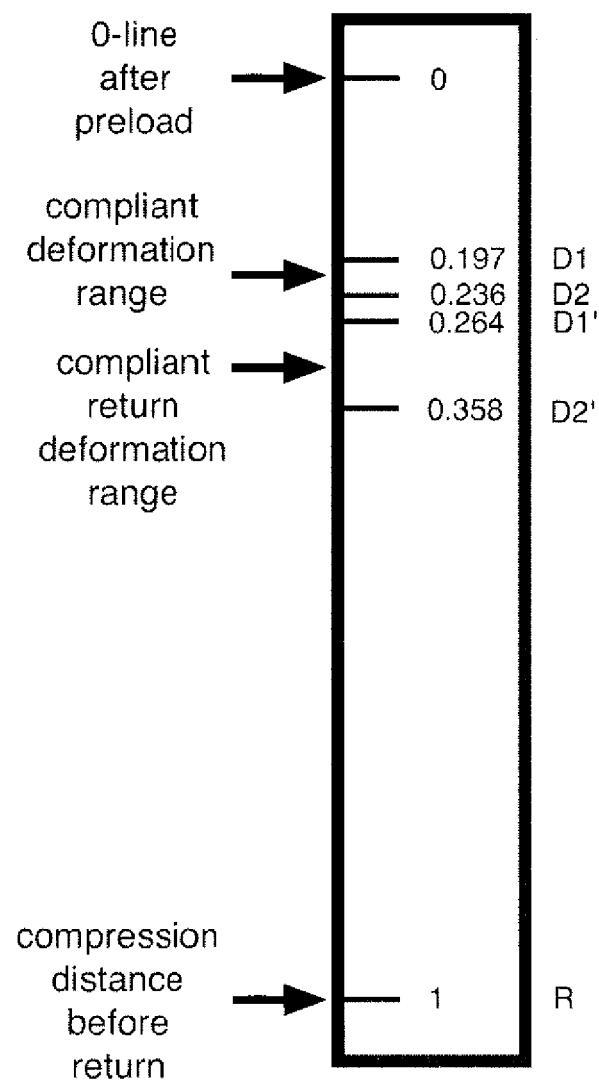
FIG. 1c is an enlarged drawing of the ruler used in the first embodiment.

A preferred embodiment of the invention, shown in FIG. 1a, consists of fixed horizontal approximately rectangular (or oval) top (1) and bottom (2) plates held in place by fixed approximately circular vertical rods (3) inserted into the centers of the outer (left and right) ends of the plates. A ball-compressing sliding element resides between the top and bottom plates. It consists of upper (4) and lower (5) horizontal approximately rectangular plates that can independently slide up and down the fixed vertical rods that pass through holes near the left and right sides of the plates. The plates are separated by a vertical spring (6) of known height and elastic constant k. (It is assumed here that the spring is linear (force ∝ distance). The use of a non-linear spring is described later.) The spring rests on the lower plate and the upper plate rests on the spring. Vertical stopping rods (7) are attached to the lower plate and a perpendicular measuring rod (8) that can move vertically resides in a hole in this plate. The stopping rods extend upwards from the lower plate to a height that is a distance d below the top of the spring, where d is chosen such that the force $f=k \cdot d$ required to compress the spring the distance d has a pre-determined value. The measuring rod can be raised or lowered through the hole in the lower plate by sliding (if the rod and accommodating hole are smooth, with the rod held in place by friction) or by rotating (if the rod and accommodating hole are threaded). A knob (9) is attached to the top of the measuring rod to facilitate the motion of the rod, and a pointer (10) (on the sliding rod) or a thin horizontal disc (on the rotating rod) is attached to the bottom of the rod to indicate the distance that the lower plate descends. The total weight of the sliding element has a pre-determined value w. (It is assumed here that w is equal to the specified preload force. The use of a sliding element whose weight is less than the preload force is described later.) A ruler (11) is attached to the bottom plate (or to one of the vertical rods) adjacent to the pointer (10) or disc attached to the bottom of the measuring rod. A zero-distance line is indicated near the top of the ruler and below this line distances D1, D2, D1', D2', and R are indicated as additional lines. (D1 is the specified minimum compliant ball compression distance when the specified force f is applied on the ball. D2 is the maximum compliant distance. D1' is the specified minimum compliant ball compression distance when the specified force f is applied on the ball after the ball has been compressed a specified distance R. D2' is the specified maximum distance when the specified force f is applied on the ball after the ball has been compressed the specified distance R. A drawing of the ruler is shown in FIG. 1c.) The final part of the embodiment is a mechanism to force the sliding element onto a ball (14) inserted between the sliding element and the bottom plate. It consists of a vertical threaded rod (12) that lowers onto the top of the upper sliding plate (4) by rotating through a threaded hole in the top plate (1), said hole being concentric with the spring (6). A turning rod (13) or arm is attached to the top of the threaded rod. (Alternative compressing mechanisms are described later.)

The use of the terms upper, lower, top, bottom, left, and right in the above description are for reference only. The device can be oriented in various directions and with various parities, and the stopping rods can be attached to the upper plate instead of the lower plate. The horizontal plates can have oval or other curved shapes instead of rectangular shapes, and the vertical rods need not be circular. The stopping rods can be threaded and inserted into threaded holes in the lower moving plate, so that the rod heights can be adjusted to accommodate springs of different heights and elasticities. The device can be used to test other standardized balls, as well as tennis balls.

Operation to Test New Balls

1. A tennis ball (14) to be tested is inserted between the bottom plate (2) and the lower sliding plate (5), centered directly under the center of the spring (6).
2. The sliding element (4-10) (of total weight w) is lowered onto the ball. (This applies the preload. See FIG. 1a.)

3. The measuring rod (8) is then lowered so that the attached pointer (10) or disc points to the zero-distance line on the ruler (11). (See FIG. 1*a*.)
4. The threaded rod (12) in the top plate (1) is then rotated downward onto the upper sliding plate (4), and then further rotated downward, causing the upper sliding plate (4) to descend, simultaneously compressing the spring (6) and ball (14), until the plate (4) touches the stopping rods (7). (See FIG. 1*b*.) (When the plate touches the stopping rods, the spring has compressed a distance d so that it exerts a force f=k·d onto the ball.)
5. The distance D that the ball (14) has compressed by the force f is then indicated by the position of the pointer (10) (or disc) on the ruler (11). (See FIG. 1*b*. The ball is potentially compliant only if $D1 \leq D \leq D2$.)
6. The threaded rod (12) in the top plate (1) is then further rotated downward until the ball is compressed a distance R, as indicated by the position of the pointer (10) (or disc) on the ruler (11).
7. The threaded rod (12) is then rotated upward until the upper sliding plate (4) begins to separate from the stopping rods (7). (At that point, the spring (6) is again compressed a distance d so the it again exerts a force f=k·d onto the ball.)
8. The distance D' that the ball has compressed by the force f is then indicated by the position of the pointer (or disc) on the ruler. (The ball is compliant only if $D1 \leq D \leq D2$ and $D1 \leq D' \leq D2'$.)

Operation to Test Used Balls

To determine if a used ball can remain in play, repeat steps 1-5. The ball is usable if $D3 \leq D \leq D4$, in terms of specified compression distances D3 and D4. The minimum compression distance D3 can have the same value as the new ball minimum D1 since a used ball cannot be stiffer than a used ball. The maximum compliant compression distance D4 can be determined by experiment. By comparing the playability of sufficiently many balls covering a range of deformation values, the appropriate D4 value will lie at the border between playable balls and unplayable balls. It is recommended that the ITF perform the necessary research and arrive at a suitable D4 value to be used in a standard for used balls.

ITF Specifications (New Type 1 Balls)
 w=15.57 N (3.5 lbs)
 f=80.07 N (18 lbs)
 D1=0.50 cm (0.197 in)
 D2=0.60 cm (0.236 in)
 R=2.54 cm (1 in)
 D1'=0.67 cm (0.264 in)
 D2'=0.91 cm (0.358 in)

Proposed New Specifications for Testing Used Balls
 D3=0.197 in
 D4=0.300 in (estimate)

Generalizations

Figure 2:
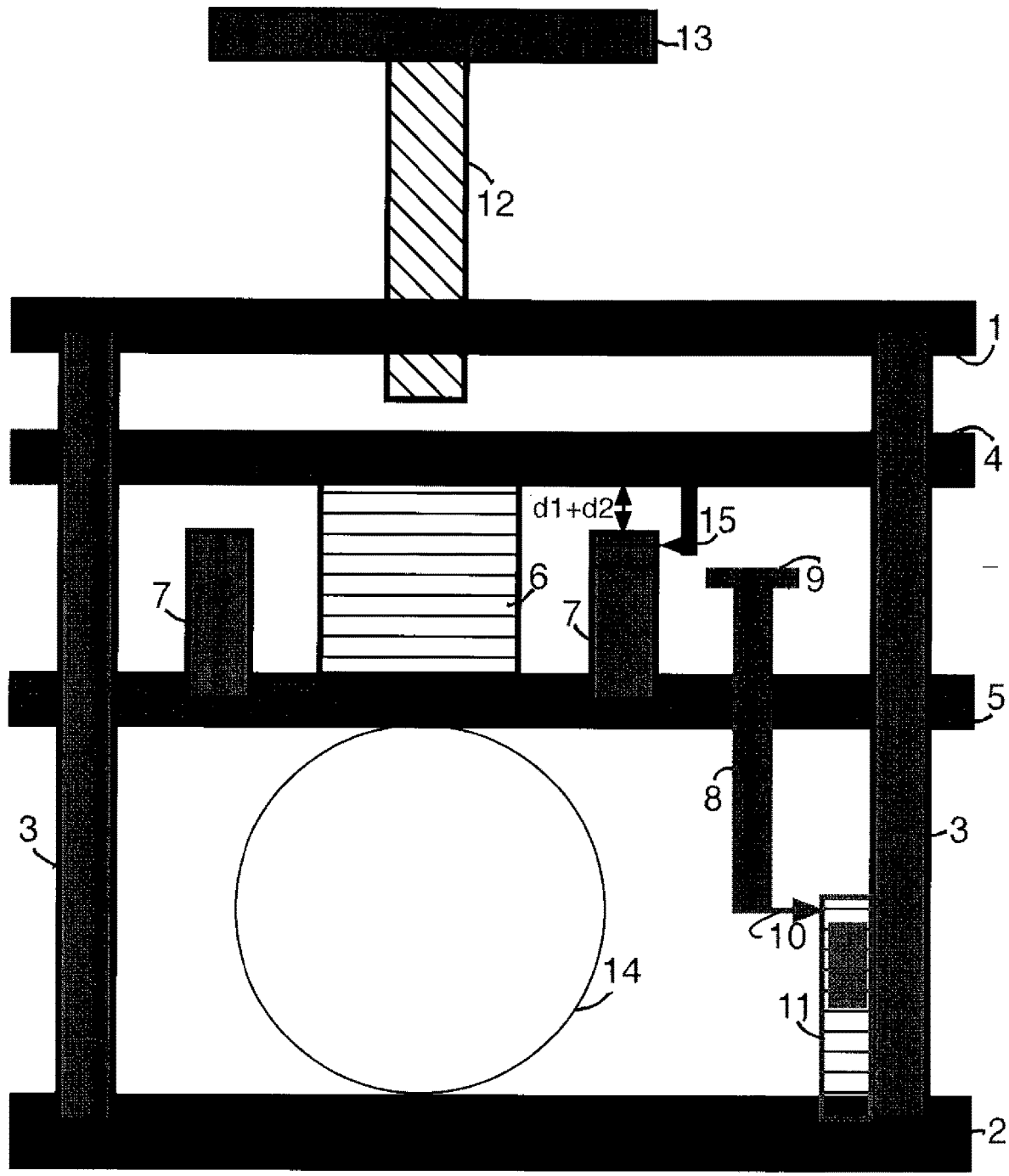
FIG. 2 is a schematic side elevational view of a modification of the portable device of FIG. 1a, in accordance with the present invention.

The weight w of the sliding element can be reduced by using the spring to supply the preload differential, i.e., by compressing the spring a distance (3.5 lbs-w)/k after the sliding element has been placed on a ball. This can be incorporated into the preferred embodiment as follows. (See FIG. 2.) A downward directed rod (15) is attached to the upper sliding plate that rests on the spring, with a pointer at the lower end pointing toward a vertical ruler attached to the lower sliding plate that lies under the spring. (The ruler can be inscribed on one of the stopping rods. See FIG. 2, #15.) Before the spring is compressed, the pointer points to a zero-distance line on the ruler. A second (lower) line on the ruler lies a distance d1=(3.5 lbs-w)/k below the zero-distance line, so that when the spring is compressed the distance d1, the force on the ball is k·d1+w=3.5 lbs, the correct preload force. After this preload is applied, the measuring rod in the lower plate is lowered so that the attached pointer or disk points at the zero-distance line on the lower ruler attached to the bottom plate. (Unlike this lower rod that measures the ball compression distance, the upper rod is permanently fixed in place because, unlike a ball, the spring has a pre-determined size and elasticity.) The stopping rods will extend upwards to a height that is a distance d1+d2 below the top of the spring, where d2=(18 lbs)/k so that the force on the ball when the upper sliding plate touches the stopping rods is k*(d1+d2)+w=18 lbs+3.5 lbs, the correct value. Although this arrangement makes the testing process slightly more complicated, it allows for a lighter testing device. (See below.) (The current ITF values of 3.5 lbs for the preload and 18 lbs for the subsequent applied force have been assumed, but the mechanism can be used for any values of these forces.)

A special case of the above generalization renders w effectively equal to zero by orienting the device in a purely horizontal direction. In this case, the entire 3.5 lb preload is supplied by the spring, with d1=(3.5 lbs)/k and d1+d2=(21.5 lbs)/k.

It was assumed in the above disclosures that the spring used in the testing device is linear. (In a linear spring, the compression force F is proportional to the compression distance x, F=k·x.) However, the inventive devices can use a spring (or equivalent) that is described by any force function F(x). All that is required is that the compression force F(x) increases when the compression distance x increases. In the preferred embodiment described above, the distance d below the top of the spring at which the stopping rods terminate is then determined by F(d)=18 lbs, instead of k·d=18 lbs. Note that, since F(x) is monotonic, the inverse function $F^{-1}(f)$ is well-defined, with $F(F^{-1}(f))$=f. The distance is thus d=$F^{-1}$ (18 lbs). The term "spring" used in this document is meant to be generic. The invented devices can use any elastic element that is characterized by a monotonically increasing force function F(x), as long as the height h and diameter b of the element, and the compression distance d=$F^{-1}$(18 lbs), are reasonable (for example, $0.5" \leq h \leq 2"$, $0.25" \leq b \leq 1.5"$, $0.25" \leq d \leq 1"$).

If a non-linear spring with monotonic force vs. distance function F(x) is used, and the sliding element weight w is less than the specified preload p, and the specified compressing force is f, then the above distance expressions are generalized to d1=$F^{-1}$(p−w) and d2=$F^{-1}$(p+f−w)−d1.

Dimensions

The preferred testing device can be constructed using conventional materials such as metallic alloys, plastics, or composite materials. Suitable dimensions for the fixed and sliding plates are 6.25" length, 2.5" width, and 0.25" thickness. Suitable dimensions for the vertical rods are 5.5" height and 0.25" diameter. Typical dimensions of the (closed-end stainless steel) spring are a height of 1.5" and a diameter of 0.75". (With an elastic constant of 36 lbs/in, a compression distance of 0.5" would then result in the specified 18 lb force.) With an initial 2.75" distance between the bottom plate and the lower sliding plate (for ball insertion), and a 0.75" gap between the top plate and upper sliding plate, the overall height of the device would then be 6", apart from the turning rod. Using aluminum plates, the sliding element would weigh about 1.5 lbs. This can be increased to the specified 3.5 lb preload by using heavier and/or thicker plate material, or by attaching a 2 lb metal block to the upper sliding plate, preferably concentric with the spring. The total weight of the device would then be about 6 lbs. If the extra 2 lbs of preload were produced by compression of the spring instead of by an attached block, the total weight would be reduced to about 4 lbs. This weight can be further reduced by using a carbon fiber composite material instead of aluminum for some of the device parts, and by using more rounded shapes for the plates instead of rectangular shapes.

Other Embodiments

Figure 3A:
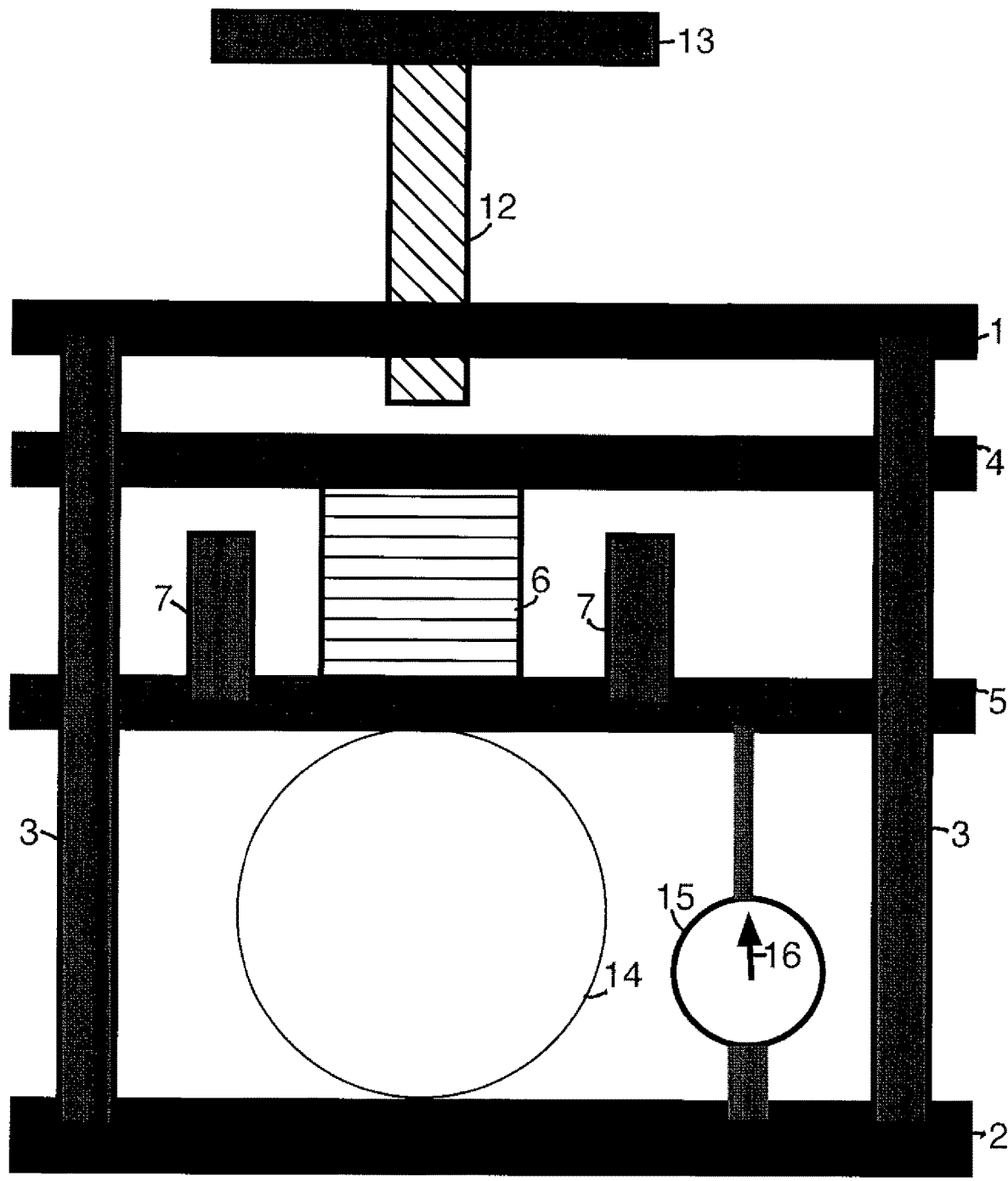
FIG. 3a is a schematic side elevational view of another embodiment of a portable device for testing a tennis ball for compliance with predetermined deformation standards, in accordance with the present invention, showing the testing device at one stage of a testing procedure.
Figure 4:
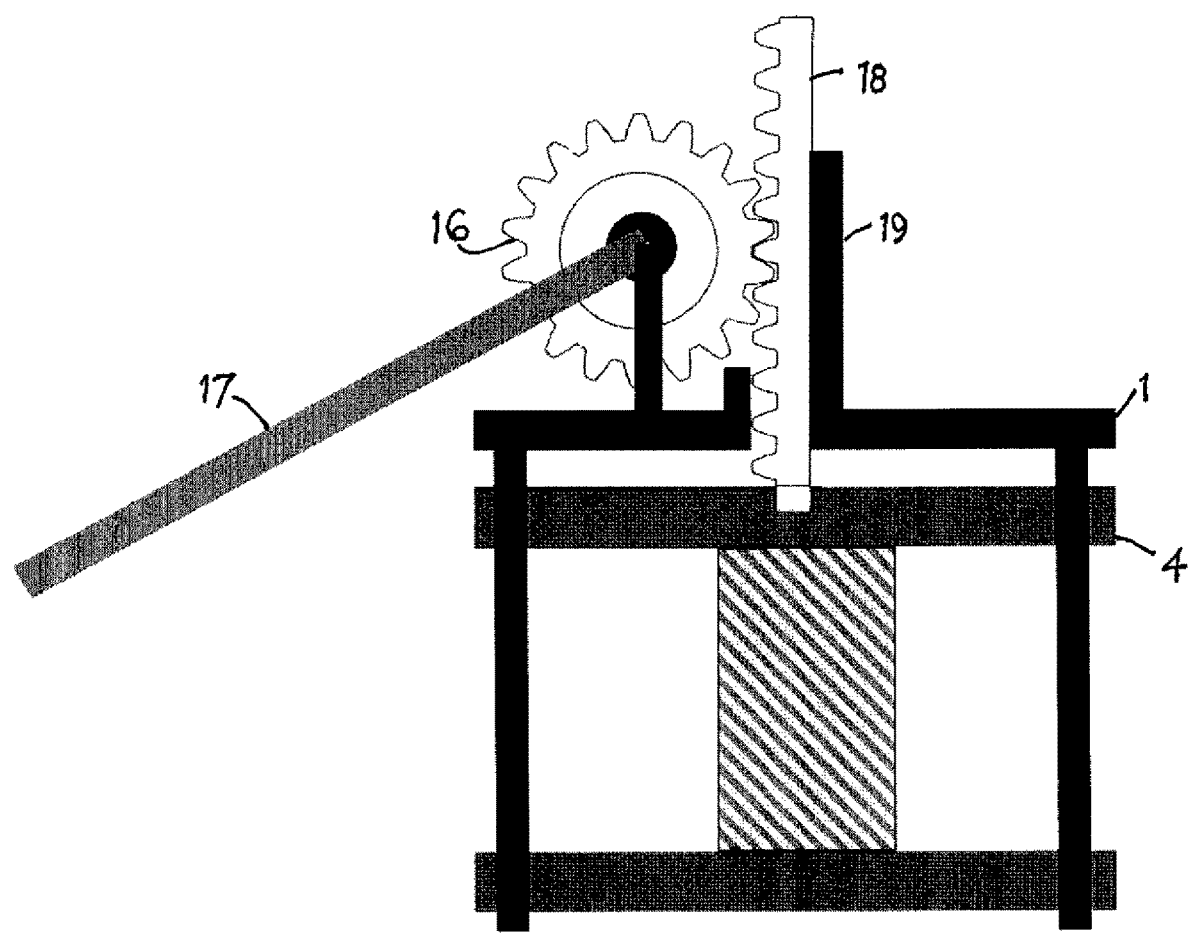
FIG. 4 is a schematic side elevational view of an upper portion of a portable device for testing a tennis ball for compliance with predetermined deformation standards, in accordance with the present invention, showing a modification of the testing device of FIGS. 1a and 1b, FIG. 2, or FIGS. 3a and 3b.

The above embodiment is a lightweight, reliable, accurate, durable, inexpensive, and easy-to-use device to test tennis balls for compliance with a stated standard. It uses no electrical or specialized mechanical components to measure forces or distances. The inventive concepts are the use of (1) a spring (or equivalent) of known size and elasticity in series with a ball to control the force exerted on the ball, (2) an adjustable pointing rod and ruler to measure the deformation of the ball, and (3) a threaded rod to force a plate onto the spring-ball system. Many other ways to implement these concepts will be apparent to those skilled in the art. Some examples are the following. The spring can be replaced by an alternative (mechanical or electrical) force gauge. The rod and ruler can be replaced by an alternative (mechanical or electrical) distance gauge. (This is illustrated in FIG. 3a.) The threaded rod can be replaced by an alternative means of force application such as a lever arm, a rack and pinion mechanism (illustrated in FIG. 4.), a hand-grip, or a pneumatic or hydraulic device.

Figure 3B:
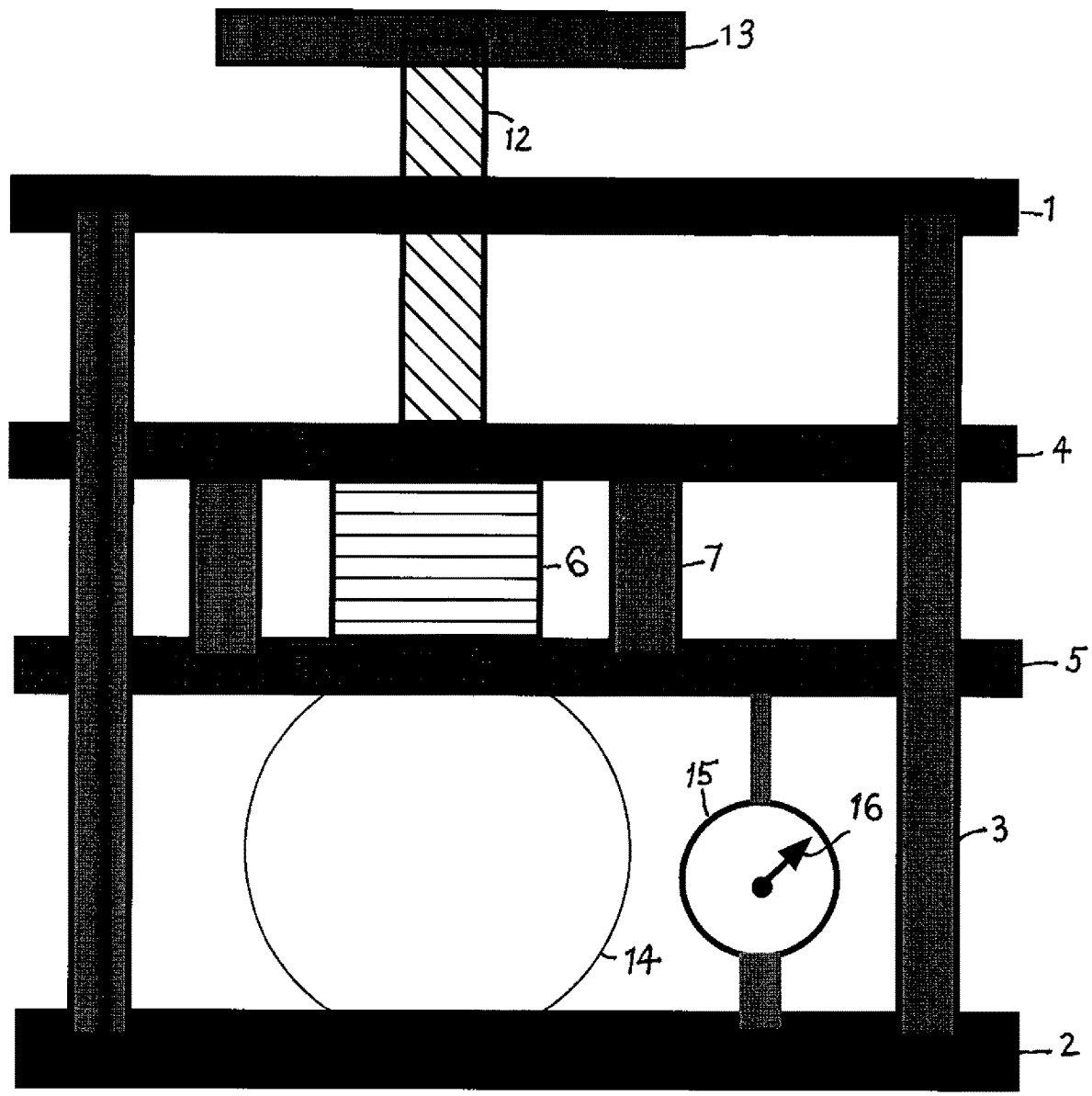
FIG. 3b is a view similar to FIG. 3a, showing the device of FIG. 3a at a different stage of a testing procedure.

If the mechanical distance gauge alternative is used, the gauge is vertically oriented and fixed to the bottom plate (or to one of the fixed vertical rods), with the retractable measurement plunger extending upward from the circular dial face element to the bottom of the lower sliding plate. The gauge face is assumed to have a central pointer pointing towards a rotatable distance scale attached around the perimeter of the dial face. The distance scale is rotatable so that any distance line can be placed adjacent to the tip of the pointer. The above ball testing operation procedure changes to the following one. (See FIGS. 3a and 3b.)

1. A tennis ball (14) to be tested is inserted onto the bottom plate (2) centered directly under the center of the spring (6).
2. The sliding element (4-7) (of total weight w) is lowered onto the ball.
3. The distance scale on the gauge (15) is then rotated so that the pointer (16) points to the zero-distance line on the dial. (See FIG. 3a.)
4. The threaded rod (12) in the top plate (1) is then rotated downward onto the upper sliding plate (4), and then further rotated downward, causing the upper sliding plate (4) to descend, simultaneously compressing the spring (6) and ball (14), until the plate (4) touches the stopping rods (7). (See FIG. 3b.) When the plate touches the stopping rods, the spring has compressed a distance d so that it exerts a force f=k·d onto the ball.)
5. The distance D that the ball (14) has compressed by the force f is then indicated by the position of the pointer on the circular distance scale. (See FIG. 3b. The ball is potentially compliant only if D1≤D≤D2.)
6. The threaded rod (12) in the top plate (1) is then further rotated downward until the ball (14) is compressed a distance R, as indicated by the position of the pointer (16) on the circular distance scale.
7. The threaded rod (12) is then rotated upward until the upper sliding plate (4) begins to separate from the stopping rods (7). (At that point, the spring (6) is again compressed a distance d so the it again exerts a force f=k·d onto the ball.)
8. The distance D' that the ball has compressed by the force f is then indicated by the position of the pointer on the circular distance scale. (The ball is compliant only if D1≤D≤D2 and D1 ≤D'≤D2'.)

If the compression force is applied by a rack and pinion mechanism instead of by a treaded rod, in a preferred embodiment (FIG. 4) the circular pinion gear (16) is attached to the top of the top plate (1), and is rotated using an attached lever arm (17). The engaged vertical rack gear (18) is positioned between the coupled pinion gear (16) and a vertical support arm (19) attached to the top of the top plate (1). It moves through a hole in the top plate so that the bottom of the rack (18) can descend onto the top of the upper sliding plate (4) and move it downward. See FIG. 4. The lever arm (17) and the rack gear (18) can be disconnected from the device for ease in transportation.

The operation of the disclosed testing devices can be modified by the incorporation of simple electrical components, at the expense of greater complexity, delicacy, and cost. For example, contact sensors or electrical circuits placed on the stopping rods can be used to indicate when the upper compression plate touches or leaves the rod tops. The movable distance-measuring rod can then be automatically lowered to the correct starting position when the plate touches the rod tops. The compression forces and deformation distances can also be measured with electrical gauges.

What is claimed is:

1. A portable device to determine if a tennis ball is compliant with a stated deformation standard, comprising:
    a first means for compressing a tennis ball by application of a pre-determined pre-load followed by a pre-determined force;
    a means for measuring the deformation of the tennis ball after it is compressed;
    a second means for compressing the tennis ball to a pre-determined distance;
    a frame;
    a rigid first plate member and a rigid second plate member in substantially parallel relationship to one another and mounted to said frame so that said first plate member is movable alternately towards and away from said second plate member, the tennis ball being compressible between said first plate member and said second plate member under a predetermined preliminary load; and
    shifting means operatively coupled with said first plate member for shifting said first plate member toward said second plate member to exert an additional force of predetermined magnitude on said tennis ball,
    said first means for compressing and said second means for compressing each including said first plate member and said second plate member,
    said means for measuring including a measuring device with a scale providing a visual indication of an amount of deformation of said tennis ball, said measuring device being mounted at least indirectly to said frame,
    said measuring device including a ruler oriented perpendicularly to said first plate member and said second plate member, said ruler being attached to one of said first plate member and said second plate member, said measuring device further including a perpendicular rod adjustably attached to the other of said first plate member and said second plate member so as to be movable transversely to said first plate member and said second plate member.

2. The device of claim 1 wherein said shifting means includes a rack and pinion mechanism, with a lever arm attached to the pinion and a perpendicular compressing plate adjacent to the lower end of the rack.

3. The device of claim 1 wherein said shifting means includes an elastic element or spring of preselected elasticity operatively coupled to said first plate member and disposed in linear alignment with said first plate member and said second plate member.

4. The device of claim 3 wherein said elastic element or spring is a compression spring disposed on a side of said first plate member opposite said second plate member, further including at least one stop element mounted at least indirectly to said frame so as to limit a compression of said compression spring to a fixed predetermined distance resulting in application of said additional force of said predetermined magnitude.

5. The device of claim 3 wherein said shifting means further includes: a rigid third plate member, said third plate member being fixed to said frame on a side of said elastic element or spring opposite said first plate member; and a rod traversing a hole in said third plate member, said rod and said hole having mating threads so that said rod is rotatable and transversely translatable relative to said third plate member.

6. The device of claim 3 wherein said stop element takes the form or one or more rods of equal height extending perpendicularly relative to said first plate and parallel to an axis of compression of said elastic element or spring.

7. The device of claim 1 wherein said perpendicular rod is threaded and rotatably traverses a threaded hole in said other of said first plate member and said second plate member, so that said perpendicular rod moves transversely to said other of said first plate member and said second plate member upon a rotation of said perpendicular rod.

8. The device of claim 7 wherein said perpendicular rod is provided with a pointer in the form of an elongate arm or a disk attached to said perpendicular rod and extending in a plane perpendicular to an axis thereof.

9. A portable device for use in determining whether a tennis ball complies with a pre-established deformation standard, comprising:
 a frame including a plurality of support rods extending in parallel relationship with one another;
 a first plate and a second plate fixed to said support rods and disposed in spaced relationship to one another;
 a ball-compressing sliding component disposed between said first plate and said second plate, said ball-compressing sliding component including:
  a third plate and a fourth plate coupled to said support rods for mutually independent sliding motion along said support rods; and
  an elastic element or spring of predetermined height and a predetermined monotonic force vs. distance function $F(x)$, said elastic element or spring being disposed between and in contact with said third plate and said fourth plate;
 means for moving said sliding component so as to compress both said elastic element or spring and a ball inserted between said second plate and one of said third plate and said fourth plate;
 means for limiting a compression distance of said elastic element or spring to $d=F^{-1}(f)$, where the force $f=F(d)$ required to compress the spring the distance d has a predetermined value; and
 means mounted at least indirectly to said support rods for measuring a degree or deformation or compression of the ball,
 wherein said sliding component has a total weight w less than or equal to a specified preload p, with the preload increased to p by compressing said elastic element or spring a measured compression distance $d1=F^{-1}(p-w)$, so that the total preload becomes $w+F(d1)=p$.

10. The device of claim 9 wherein a downwardly directed rod attached to the upper one of said third plate and fourth plate is provided for measuring the compression distance d1, said downwardly directed rod having a pointer at a lower end pointing toward a vertical ruler attached to a lower one of said third plate and said fourth plate, said downwardly directed rod and said pointer being configured so that said pointer points to a zero-distance line on said ruler before said elastic element or spring is compressed, said ruler being marked with a distance d1 so that the preload force is specified preload p when the elastic elements or spring is compressed the distance d1, as indicated by the pointer pointing to the d1 line.

11. The device of claim 10 wherein the means for limiting the compression distance of said elastic element or spring includes one or more stopping rods that extend upwards from the lower of said third plate and said fourth plate to a height that is a distance d1+d2 below an upper end of the elastic element or spring, where $$d2=F^{-1}(p+f-w)-d1,$$

so that the force on the ball when the spring compression terminates on the stopping rods is $F(d1+d2)+w=p+f$, the specified applied force value when the ball compression distance is measured to test for compliance with the stated standard.

12. The device of claim 9 wherein the means for moving said sliding component includes a rod traversing a hole in said first plate, said rod having one end in force-transmitting engagement with said third plate, said hole being coaxial with said elastic element or spring.

13. The device of claim 9 wherein the means for limiting the spring compression distance includes one or more stopping rods attached to one of said third plate and said fourth plate and extending towards the other of said third plate and said fourth plate, said one or more stopping rods having a length preselected so as to arrest relative motion of said third plate and said fourth plate upon compression of said elastic element or spring by a predetermined distance d.

14. The device of claim 9 wherein said support rods are oriented vertically, said first plate, said second plate, said third plate and said fourth plate all extending in respective horizontal planes in parallel to each other.

15. The device of claim 9 wherein said means for moving said sliding component includes a rack and pinion mechanism, said rack and pinion mechanism including a rotatable pinion attached to an upper one of said first plate and said second plate, said rack and pinion mechanism further including a lever arm attached to the rotatable pinion, said rack and pinion mechanism also including a rack movable through a hole in said upper one of said first plate and said second plate so that a lower end of said rack is engageable with an upper surface of an upper one of said third plate and said fourth plate to move same downwardly.

16. A portable device for use in determining whether a tennis ball complies with a pre-established deformation standard, comprising:
 a frame including a plurality of support rods extending in parallel relationship with one another;

a first plate and a second plate fixed to said support rods and disposed in spaced relationship to one another;

a ball-compressing sliding component disposed between said first plate and said second plate, said ball-compressing sliding component including:

a third plate and a fourth plate coupled to said support rods for mutually independent sliding motion along said support rods; and an elastic element or spring of predetermined height and a predetermined monotonic force vs. distance function F(x), said elastic element or spring being disposed between and in contact with said third plate and said fourth plate;

means for moving said sliding component so as to compress both said elastic element or spring and a ball inserted between said second plate and one of said third plate and said fourth plate;

means for limiting a compression distance of said elastic element or spring to $d=F^{-1}(f)$, where the force $f=F(d)$ required to compress the spring the distance d has a predetermined value; and means mounted at least indirectly to said support rods for measuring a degree or deformation or compression of the ball, the means for measuring the deformation of the ball including a measuring rod movably traversing a hole in said fourth plate, said measuring rod being provided with a pointer in the form of an elongate arm or a disk attached to said measuring rod and extending in a plane perpendicular to an axis thereof.

17. A portable device for use in determining whether a tennis ball complies with a pre-established deformation standard, comprising:

a frame including a plurality of support rods extending in parallel relationship with one another;

a first plate and a second plate fixed to said support rods and disposed in spaced relationship to one another;

a ball-compressing sliding component disposed between said first plate and said second plate, said ball-compressing sliding component including:

a third plate and a fourth plate coupled to said support rods for mutually independent sliding motion along said support rods; and an elastic element or spring of predetermined height and a predetermined monotonic force vs. distance function F(x), said elastic element or spring being disposed between and in contact with said third plate and said fourth plate;

means for moving said sliding component so as to compress both said elastic element or spring and a ball inserted between said second plate and one of said third plate and said fourth plate;

means for limiting a compression distance of said elastic element or spring to $d=F^{-1}(f)$, where the force $f=F(d)$ required to compress the spring the distance d has a predetermined value; and means mounted at least indirectly to said support rods for measuring a degree or deformation or compression of the ball, further comprising:

a measuring rod attached to said third plate and extending towards said fourth plate for measuring a compression distance of said elastic element or spring, said measuring rod being provided at one end with a pointer;

an elongate marker member attached to said fourth plate and extending toward said third plate, said elongate marker member being provided with a zero-distance mark, said pointer being aligned with said zero-distance mark prior to compression of said elastic element or spring, said elongate marker member being further provided with a distance d1 mark, so that a preload force takes on a predetermined initial value upon a compressing of said elastic element or spring the distance d1, as indicated by the pointer pointing to the distance d1 marker.

18. A method for determining whether a tennis ball is compliant with a predetermined deformation standard, comprising:

providing a device including a frame, a rigid first plate member and a rigid second plate member, first plate member and said second plate member being disposed in substantially parallel relationship to one another and mounted to said frame so that said first plate member is movable alternately towards and away from said second plate member;

inserting the tennis ball between said first plate member and said second plate member;

upon inserting said tennis ball between said first plate member and said second plate member, moving said first plate member towards said second plate member to place said tennis ball under a predetermined preliminary load;

shifting said first plate member further toward said second plate member to exert an additional force of predetermined magnitude on said tennis ball; and visually reading an indicator position relative to a scale element mounted to said frame, said indicator position providing an indication of an amount of deformation of said tennis ball, wherein the visual reading of said indicator position includes setting a pointer on a rod at a zero-distance mark on said scale element before said tennis ball is compressed, and reading a position of said pointer on said scale element after said tennis ball is compressed.

19. The method of claim 18 wherein said scale element is provided with a first additional mark for a specified minimum compliant ball compression distance when a specified force is applied to said tennis ball, a second additional mark for a maximum compliant distance, a third additional mark for a specified minimum compliant ball compression distance when the specified force is applied to said tennis ball after said tennis ball is compressed a specified distance, and a fourth additional mark for a specified maximum distance when the specified force is applied to said tennis ball after said tennis ball is been compressed the specified distance.

* * * * *